United States Patent [19]

Strittmatter

[11] Patent Number: 5,910,629
[45] Date of Patent: Jun. 8, 1999

[54] CHIMERIC GENES COMPRISING A FUNGUS-RESPONSIVE ELEMENT

[75] Inventor: Günter Strittmatter, Cologne, Germany

[73] Assignee: Max-Planck-Gesellschaft zur Forderung der Wissenschaften E.V., Munich, Germany

[21] Appl. No.: 08/737,298

[22] PCT Filed: Mar. 9, 1995

[86] PCT No.: PCT/EP95/00868

§ 371 Date: Jan. 6, 1997

§ 102(e) Date: Jan. 6, 1997

[87] PCT Pub. No.: WO96/28561

PCT Pub. Date: Sep. 19, 1996

[51] Int. Cl.$^6$ .............................. A01H 5/00; C12N 15/29; C12N 15/82; C12N 5/04

[52] U.S. Cl. .................... 800/279; 800/265; 800/268; 800/285; 800/287; 800/298; 435/69.1; 435/418; 435/419; 435/468; 536/23.6; 536/24.1; 536/24.5

[58] Field of Search ................... 536/23.6, 24.1, 536/24.5; 435/69.1, 172.3, 418, 419, 468; 800/205, 250, 265, 268, 279, 285, 287, 298

[56] References Cited

FOREIGN PATENT DOCUMENTS 9319188  9/1993  WIPO .

OTHER PUBLICATIONS

J. Cell. Biochem., vol. 19B, 1995, pp. 161, Abstract No. B4–224, G. Strittmatter et al.

Mol. Gen. Genet., vol. 236, 1993, pp. 179–186, N. Martini et al.

*Primary Examiner*—David T. Fox
*Attorney, Agent, or Firm*—Birch, Stewart, Kolasch & Birch, LLP

[57] ABSTRACT

The present invention provides improved fungus-responsive chimeric genes for the production of transgenic plants which have plant cells surrounding the site of fungal infection that become capable of killing, disabling or repelling the fungus or that are themselves killed or rendered unsuitable for the fungus to feed upon, thereby preventing the spread of the fungus infection.

27 Claims, 1 Drawing Sheet

CHIMERIC GENES COMPRISING A FUNGUS-RESPONSIVE ELEMENT

FIELD OF THE INVENTION

This invention relates to the use, in a transgenic plant, of newly-identified fungus-responsive elements of the prp1-1 promoter (fungus-responsive prp1-1 elements) to induce, in response to a fungus infection of the plant, the expression of a DNA fragment substantially selectively in cells of the plant around the site of the fungal infection. The use of the fungus-responsive prp1-1 elements of this invention is especially valuable in transgenic plants for controlling a foreign DNA fragment that is to be expressed selectively in the cells of the plant which immediately surround the fungal infection site.

This invention further relates to a first or fungus-responsive chimeric gene that can be used to transform a plant and that comprises a first foreign DNA that:

a) encodes a product which, when expressed in cells of the plant immediately surrounding a fungal infection site, can either i) kill or at least disable the plant cells immediately surrounding the fungal infection site or ii) kill, disable or repel one or more fungi in the fungal infection site; and b) is under the control of a promoter comprising at least one fungus-responsive prp1-1 element.

This invention further relates to a cell of a plant, the genome of which is transformed to contain the first chimeric gene and optionally a second or restorer chimeric gene; the second chimeric gene contains a second promoter that controls a second foreign DNA encoding a product which allows the inhibition or inactivation of the first foreign DNA or its encoded product at least in cells of the plant other than those immediately surrounding a fungal infection site, particularly when the first foreign DNA encodes a product that can kill or adversely disturb such other plant cells.

This invention yet further relates to: a) the fungus-resistant transgenic plant, such as a Solanaceae (e.g., tomato or potato) or Brassicaceae (e.g., oilseed rape) plant, which is regenerated from the plant cell of this invention transformed with the first and optionally the second chimeric gene of this invention, b) fungus-resistant transgenic plants derived from the regenerated transgenic plant and seeds of such plants, and c) plant cell cultures comprising the transformed plant cells of this invention.

The plants of this invention are characterized by the fungus-responsive expression of the first chimeric gene of this invention in plant cells surrounding, preferably immediately surrounding, the fungal infection site and either:

a) the substantial, preferably complete, absence of expression of the first chimeric gene in all other plant cells; or b) the substantial absence and preferably the complete absence, e.g., by expression of the second chimeric gene of this invention, of the effects of any expression of the first chimeric gene in all other plant cells—thereby rendering the plants resistant to fungal infections.

BACKGROUND OF THE INVENTION

The fungi are a very old group of microorganisms. Harmful fungi cause diseases of man, other animals, and especially plants. About 8000 species of fungi can cause plant diseases, and all plants are attacked by some kind of fungi. Some plant-pathogenic fungi can attack many plant species, others attack only one.

In general, fungal plant diseases can be classified into two types: those caused by soilborn fungi and those caused by airborn fungi. Soilborn fungi cause some of the most widespread and serious plant diseases, such as root and stem rot caused by Fusarium spp. and root rot caused by Phytophthora spp.

Since airborn fungi can be spread long distances by wind, they can cause devastating losses, particularly in crops which are grown over large regions. A number of these pathogens have caused widespread epidemics in a variety of crops. Important diseases caused by airborn fungi are stem rust (*Puccinia graminis*) on wheat, corn smut (*Ustilago maydis*) on corn, and late blight disease (*Phytophthora infestans*) on potato and tomato.

Most of these fungal diseases are difficult to combat, and farmers and growers must use a combination of practices, such as sanitary measures, resistant cultivars, and effective fungicides, against such diseases. Hundreds of million dollars are spent annually for chemical control of plant-pathogenic fungi. As a result, there is today a real need for new, more effective and safe means to control plant-pathogenic fungi.

It is known that plants possess defense mechanisms against fungal diseases. When a plant recognizes a fungal attack, it can respond by inducing several reactions in its cells immediately surrounding the fungal infection site. Resistance mechanisms are activated by the initial infection, so as to limit the spread of the invading fungal pathogen (Ward et al, 1991). The resistance mechanisms include a localized cell death known as a hypersensitive response, the accumulation of phytoalexins, and lignification (De Wit, 1987). The specificity of these responses, which can be very effective in limiting the spread of a fungal infection, depends on the genetic make-up of the host and the pathogen.

Characterization of the genetic components which control cultivar/race specific host/pathogen interactions is a goal of current molecular plant pathology research. Transcriptional activation of defense-related genes is part of the complex defense system which enables plants to deal with contacts with potential pathogens (Collinge and Slusarenko, 1987; Hahlbrock and Scheel, 1989; Bowles, 1990). The identification of cis-acting elements regulating the expression of defense-related genes has been sought in order to elucidate the process by which signal transduction chains connect the initial recognition of a pathogen by a plant host with its induction of defense reactions (Lamb et al, 1989). As found for several other host/pathogen systems (van Loon, 1985; Hahlbrock and Scheel, 1989), infection of potato with the fungus *Phytophthora infestans*, which is the causal agent of late blight disease, leads to transcriptional activation of genes encoding enzymes of the phenylpropanoid metabolism and PR-proteins (Fritzemeier et al, 1987; Kombrink et al, 1988; Taylor et al, 1990). Transcription of these genes is induced with similar kinetics in compatible and incompatible interactions of different potato cultivars with different *Phytophthora infestans* races. The nucleotide and deduced amino acid sequences of one of the "pathogenesis related" (or "PR")-protein genes in potato, i.e., prp1-1, which is a member of the large prp1 gene family (with 10–15 very similar copies per haploid genome), shows striking similarity to the corresponding sequences of a gene encoding the HSP26 heat-shock protein in soybean (Taylor et al, 1990). In situ hybridization experiments showed that the PRP1-1 transcript accumulates around the site of fungal penetration, but the function of this protein in the defense strategy of potato is not yet clear. The homologous soybean HSP26 protein represents a unique member within a group of low molecular weight heat-shock proteins of plants, appearing in an unusually high relative concentration under a broad variety of stress conditions (Czarnecka et al, 1984; Vierling, 1991) but also having no known role in cell metabolism. No sequence similarity has been found between the protein encoded by the prp1-1 gene and several known PR-proteins from other Solanaceous species (Taylor et al, 1990). In PCT patent publication WO 93/19188 and Martini et al. (1993), which are both incorporated herein by reference, a 273 basepairs (bp) fragment of the prp1-1 promoter was found to still induce local expression of a DNA sequence upon fungal infection, but, in contrast to the native prp1-1 promoter, this promoter element was found not to be induced by heavy metal salts.

Most plant genes encoding proteins related to pathogen defense, analyzed to date on the level of cis-acting elements, are also activated by several other stress stimuli like mechanical wounding, light and/or elevated concentrations of heavy metals (Oshima et al, 1990; Schmid et al, 1990; Stermer et al, 1990; Douglas et al, 1991; Joos and Hahlbrock, 1992). In a plant-nematode interaction, a part of the tobacco RB7 promoter was found to confer selective and local expression in the nematode feeding structures induced in the roots upon infection by certain nematodes (Opperman et al., 1994).

Recent reports show that certain levels of resistance towards fungal pathogens can be obtained by expressing antifungal proteins in transgenic plants. Examples include the expression of a chitinase either alone (Benhamou et al., 1993) or in combination with a glucanase (Zhu et al., 1994), the expression of osmotin (Liu et al., 1994), or the expression of certain PR proteins (Alexander et al., 1993).

SUMMARY OF THE INVENTION

In accordance with this invention are provided portions of the prp1-1 promoter region, which can still induce expression of a chimeric gene upon fungal infection but have a substantial lower expression in roots and/or are significantly less induced by phytohormone application when compared to the DNA sequence of SEQ ID No. 1, preferably portions of the prp1-1 promoter region, which can still induce expression of a chimeric gene upon fungal infection but which have substantially lost their expression in roots and have a significantly lower responsiveness to phytohormone application.

Further in accordance with this invention are provided fungus-responsive prp1-1 elements, derived directly or indirectly from the DNA sequence of SEQ ID No. 1, but lacking the nucleotides from positions 1 to 100 in SEQ ID No. 1, or lacking the nucleotides from positions 239 to 273 in SEQ ID No. 1., or fungus-responsive prp1-1 elements, derived directly or indirectly from the DNA sequence of SEQ ID No. 1, and:

a) comprising a nucleotide sequence from a position between nucleotide position 100 and 176 to nucleotide position 273 of SEQ ID No. 1, provided that said fungus-responsive element is not the DNA sequence of SEQ ID No. 1, or b) comprising the DNA sequence of nucleotide position 1 to a position between nucleotide positions 153 and 239 in SEQ ID No. 1; provided that said fungus-responsive element is not the DNA sequence of SEQ ID No. 1.

Most preferred fungus-responsive prp1-1 elements are those selected from the group of: the DNA sequence of SEQ ID No. 1 from nucleotide position 1 to 239, the DNA sequence of SEQ ID No.1 from nucleotide position 1 to 153, the DNA sequence of SEQ ID No. 1 from nucleotide position 100 to 273, the DNA sequence of SEQ ID No. 1 from nucleotide position 140 to 273 and the DNA sequence of SEQ ID No. 1 from nucleotide position 176 to 273, as well as any fungus-responsive element with substantially the same nucleotide sequence, so that the DNA sequence has essentially the same promoter activity.

Also provided herein is a fungus-responsive promoter, comprising any of the newly identified fungus-responsive prp1-1 elements, provided this fungus-responsive promoter does not comprise the DNA sequence of FIG. 1.

Further encompassed in this invention are fungus-responsive chimeric genes, which comprise, besides the fungus-responsive promoter of this invention, a first foreign DNA that encodes a first RNA and/or protein or polypeptide which, when produced or overproduced in the cells of the plant which surround, preferably immediately surround, said fungus-infection site, a) kills, disables or repels said fungus, or b) kills, or at least disturbs significantly the metabolism, functioning and/or development of the plant cells surrounding, preferably immediately surrounding, said fungus-infection site, so as to limit further spread of said fungus; and suitable 3' transcription termination signals for expressing said first foreign DNA in the cells of the plant which surround, preferably immediately surround, said fungus infection site.

Also in accordance with this invention is provided a cell of a plant, in which the nuclear genome has been transformed to contain the first chimeric gene of this invention and optionally—especially when the first foreign DNA is of type b) above—to contain also the second or restorer chimeric gene, preferably in the same genetic locus; the second chimeric gene comprises the following, operably linked, DNA sequences:

1) a second promoter, such as a fungus-repressed promoter, which can direct transcription of a foreign DNA in at least cells of the plant other than those surrounding, preferably other than those immediately surrounding, the fungus infection site;

2) a second foreign DNA that encodes a second RNA and/or protein or polypeptide which, when produced or overproduced in at least such other cells of the plant, inhibits or inactivates the first foreign DNA or the first RNA or protein or polypeptide in at least said other cells of the plant; and 3) suitable 3' transcription termination signals for expressing the second foreign DNA in at least such other cells of the plant.

Further in accordance with this invention are provided: the fungus-resistant plant regenerated from the transformed plant cell of this invention, fungus-resistant plants and seeds derived therefrom, and plant cell cultures, each of which comprises the transformed plant cells of this invention.

Still further in accordance with this invention is provided a process for rendering a plant resistant to one or more fungi, particularly plant-pathogenic fungi such as Phytophthora (e.g., *P. infestans*) and Cladosporium (e.g., *Cladosporium fulvum*), Pythium spp, Fusarium spp, Sclerotinia spp, Puccinia spp, Ustilago spp, Altemaria spp, Helminthosporium spp., Septoria spp, Pyrenophora spp, Botrytis spp, Erysiphe spp., as well as *Pyrenoperiza brassicae, Cylindrosporium concentricum, Phoma lingam, Leptosphaeria maculans, Sclerotinia sclerotoirum, Botrytis cinerea, Erysiphe cruciferorum, Peronospora parasitica, Plasmodiophora brassicae*, and *Pseudocercosporella capsella*, comprising the step of transforming the plant's nuclear genome with the first or fungus-responsive chimeric genes of the invention and optionally with the second chimeric gene of this invention.

Figure 1:
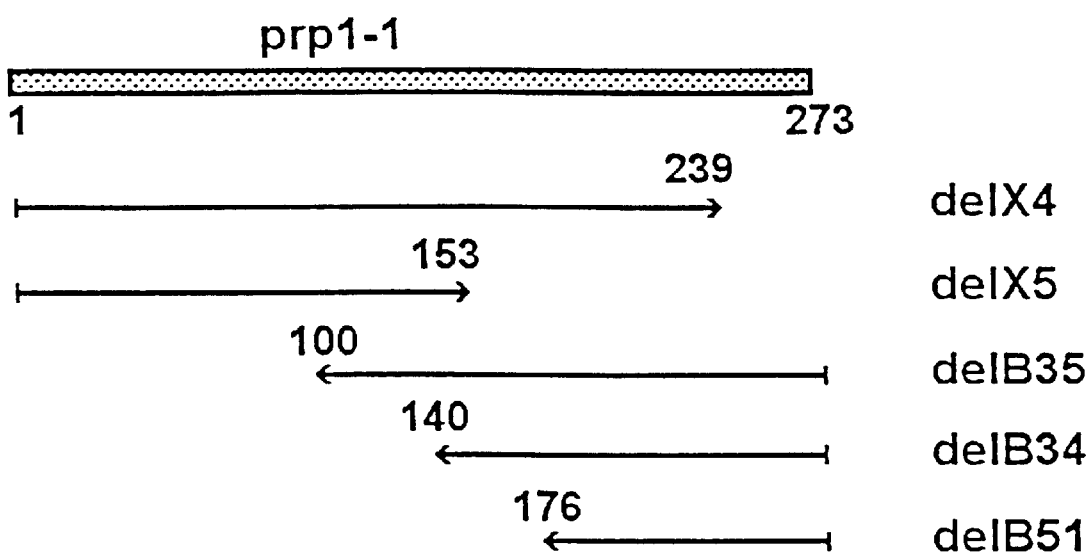
FIG. 1

Schematical overview of the deletion fragments of the 273 bp prp1-1 promoter. The nucleotide positions indicated refer to the positions in the 273 bp promoter, corresponding to positions −402 to −130 of the native prp1-1 promoter of Martini et al (1993).

DETAILED DESCRIPTION OF THE INVENTION

Throughout this Description and the Claims, the following definitions apply:

"Fungus-infected plant", as used herein, is a plant which is infected by at least one fungus species, particularly a plant-pathogenic fungus species, such as Phytophthora spp, Cladosporium spp. Pythium spp, Fusarium spp, Sclerotinia spp, Puccinia spp, Ustilago spp, Altemaria spp, Helminthosporium spp., Septoria spp, Pyrenophora spp, Ustilago spp, Botrytis spp, Erysiphe spp., as well as *Pyrenoperiza brassicae. Cylindrosporium concentricum, Phoma lingam, Leptosphaeria maculans, Sclerotinia sclerotiorum, Botrytis cinerea, Erysiphe cruciferorum, Peronospora parasitica, Plasmodiophora brassicae*, and *Pseudocercosporella capsella* and the like.

"Promoter", as used herein, refers to a DNA sequence which is recognized and bound (directly or indirectly) by a DNA-dependent RNA polymerase during initiation of transcription. A promoter includes the transcription initiation site, and binding sites for transcription initiation factors and RNA polymerase, and can comprise various other sites at which gene regulatory proteins may bind. The "prp1-1 promoter", as used herein, refers to the native promoter sequence of the prp1-1 gene, also suggested to be named gst1 (Hahn & Strittmatter, 1994), characterized by the partial sequence described in FIG. 3 of Martini et al. (1993). The "273 bp prp1-1 promoter", as used herein, refers to the 273 bp fragment of the prp1-1 promoter, described by Martini et al. (1993) as being sufficient for rapid and strictly localized transcriptional activation at fungal infection sites. This 273 bp prp1-1 promoter is represented in SEQ ID No. 1.

"Fungus-responsive promoter", as used herein, refers to a promoter, whose action in controlling transcription of a DNA sequence in a plant: 1) is induced (i.e., stimulated) by infection of the plant by a fungus, particularly a plant-pathogenic fungus; and 2) occurs substantially selectively, preferably exclusively, in plant cells around the fungal infection site, preferably in plant cells immediately surrounding the fungal infection site.

"Fungus-repressed promoter", as used herein, refers to a promoter, whose action in controlling transcription of a DNA sequence (e.g., a gene) in a plant is locally repressed (i.e. partially or fully inhibited) upon infection of the plant by a plant-pathogenic fungus, and this repression occurs substantially selectively, preferably exclusively, in those plant cells around the fungal infection site, particularly in those plant cells immediately surrounding the fungal infection site. Preferably, this promoter is otherwise constitutively expressed throughout the plant but locally repressed at the site of fungal infection.

"Plant promoter" or "plant-expressible promoter", as used herein, refers to a promoter sequence capable of driving transcription in a plant cell. This includes any promoter of plant origin, as well as any promoters foreign to plants but also allowing transcription in plant cells, i.e., certain promoters from viral or bacterial origin such as the T-DNA and 35S or 19S promoters.

"Fungus-responsive element", as used herein in relation to a fungus-responsive promoter, is that element or part of a promoter that is responsible for the fungus-responsiveness of the promoter. A promoter can have several fungus-responsive elements, besides a minimal promoter element and enhancer regions. Preferred fungus-responsive elements, in accordance with this invention, are the fungus-responsive prp1-1 elements of Example 1, as represented in FIG. 1.

"Artificial hypersensitive cell death" refers to a plant defense mechanism which is conferred by a first chimeric gene of this invention on a plant transformed therewith and which involves necrosis of plant cells at a pathogen infection site, thereby limiting further spread of the pathogen. This mechanism is analogous to a natural hypersensitive cell death occurring in incompatible plant/pathogen interactions.

"Foreign" with regard to a DNA sequence, such as a first or second foreign DNA of this invention, means that such a DNA is not in the same genomic environment (e.g., not operably linked to the same promoter and/or 3' end) in a plant cell, transformed with such a DNA in accordance with this invention, as is such a DNA when it is naturally found in a cell of the plant, bacterium, animal, fungus, or in a virus or the like, from which such a DNA originates. Foreign DNA, in accordance with this invention, thus includes DNA that is originally found in a plant genome, but which has been inserted in a different genomic locus or site compared to the endogenous DNA (see also the definition on page 5 of European patent publication (EP) 0 344 029 in this respect).

"Fungus-resistant plant", as used herein, refers to a plant displaying increased tolerance to infection with a fungal pathogen, as can be determined by routine fungal infection analysis, e.g., the method described in WO 93/19188. A fungus-resistant plant typically has better agronomical performance, e.g., yield, under conditions of fungal attack when compared to the wild-type plants.

"Selective expression", as used herein in relation to the fungus-responsive prp1-1 elements of this invention, means expression with high specificity in the plant cells surrounding, preferably immediately surrounding, the fungal infection site. The term selective expression, as used herein, does not exclude that some expression can occur in other cells of a plant during a certain developmental stage (e.g., in nonessential plant cells), nor does this definition require that the promoter portions have to be exclusively induced by a fungal pathogen.

"Cells immediately surrounding the fungal infection site", as used herein, refers to those cells that are located in the close vicinity of the fungus. Preferably, the cells immediately surrounding the fungal infection site are those cells that, when killed or negatively affected by the local expression of a first chimeric gene of this invention, (directly or indirectly) prevent the further growth and spread of the fungus.

"Essential plant cells", as used herein, refers to those cells of a plant that negatively affect the yield or value of a plant as an agricultural crop when they would be destroyed or when their function would be inhibited. Indeed, some cells in a plant are not essential to the economic value of the plant, such as the cells in a potato flower in a European potato tuber production field, or the pollen cells in the anthers of plants sold as cut flowers, or some cells in a tissue whose death or disfunctioning does not affect the functioning of this tissue.

In accordance with this invention, portions of the 273 bp prp1-1 promoter have been identified that are more selectively induced by fungal pathogens, i.e., that have substantially lost the root expression and/or are significantly less induced by phytohormone application, while still conferring local induction of expression upon fungal infection. The term "fungus-responsive prp1-1 elements", as used herein, refers to the newly identified fungus-responsive promoter elements, being portions of the 273 bp prp1-1 promoter of WO 93/18199 (represented in SEQ ID No. 1) that retain significant fungus-responsiveness but have improved characteristics such as a loss of non-target expression and/or a lower responsiveness to phytohormone application. Included in this definition of fungus-responsive prp1-1 elements is any portion(s) of the 273 bp prp1-1 DNA of SEQ ID No.1, provided that the transcription from a promoter, comprising this portion, is significantly less induced upon phytohormone application and/or is substantially lower in roots, when compared to the 273 bp prp1-1 promoter. Preferably these fungus-responsive prp1-1 elements retain less than about 5%, more preferably less than about 2 to 4% of the phytohormone responsiveness of the 273 bp prp1-1 DNA of SEQ ID No.1, and preferably have a histochemically non-detectable expression in roots, as identified by GUS-linked marker gene analyses as shown in Example 2.

Deletion analyses of the 273 bp prp1-1 promoter showed that the root expression of the 273 bp prp1-1 promoter resides in the portion of nucleotide 239 to 273 of the partial prp1-1 DNA sequence of SEQ ID No. 1. Concomitantly, fungus-responsive promoters can be devised that are obtained from the prp1-1 promoter but that lack significant expression in roots by deletion, substitution or alteration of this part. This deletion analyses has also shown that a fungus-responsive prp1-1 element still induced by fungal infection but significantly less induced by phytohormones such as salicylate and indole acetate is situated between nucleotide positions 176 and 273 in SEQ ID No. 1. Thus, preferred fungus-responsive prp1-1 elements of this invention are promoter elements derived directly (i.e., by applying routine molecular biological techniques to the DNA sequence represented in SEQ ID No. 1) or indirectly (i.e., hypothetically obtainable from the DNA sequence of SEQ ID No. 1; for example, in vitro DNA synthesis) from the DNA sequence of SEQ ID No. 1, but lacking the nucleotides from positions 1 to 100 in SEQ ID No. 1, preferably promoter elements obtained or derived directly or indirectly from the DNA sequence of SEQ ID No. 1 but lacking the nucleotides from positions 239 to 273 in SEQ ID No. 1. Alternatively, the DNA sequence between nucleotide position 1 to 100 or between nucleotides 239 to 273 in SEQ ID No.1 can be rendered non-functional by deletion, addition or replacement of nucleotides (e.g., site-directed mutagenesis) to obtain a preferred fungus-responsive prp1-1 element derived from the DNA sequence of SEQ ID No. 1 in accordance with this invention.

Preferred fungus-responsive prp1-1 elements, in accordance with this invention, are those which comprise the DNA sequence of SEQ ID No. 1 from a nucleotide position between nucleotide positions 100 and 176 to nucleotide position 273, or which comprise the DNA sequence of SEQ ID No. 1 from nucleotide position 1 to a position between nucleotide positions 153 and 239 in SEQ ID No. 1 as their fungus-responsive element, provided that these fungus-responsive promoters do not comprise the DNA sequence of SEQ ID No. 1 as its fungus-responsive element or have a significantly lower phytohormone-responsiveness and/or a substantially lower expression in roots when compared to the 273 bp prp1-1 promoter.

Particularly preferred fungus-responsive prp1-1 elements of this invention are those termed delB34 (nucleotide positions 140 to 273 in SEQ ID No. 1), delB35 (nucleotide positions 100 to 273 in SEQ ID No. 1), and delB51 (nucleotide positions 176 to 273 in SEQ ID No. 1), that are significantly less responsive to salicylic acid and indolyl acetate application (2- to 3-fold lower induction) when compared to the 273 bp prp1-1 promoter, even more preferred fungus-responsive prp1-1 elements of this invention are those termed delX4 (nucleotide positions 1 to 239 in SEQ ID No. 1) and delX5 (nucleotide positions 1 to 153 in SEQ ID No. 1), since these portions have substantially (i.e., drastically) lost the expression observed in root tips with the 273 bp prp1-1 promoter (WO 93/119188, e.g., no histochemically detectable GUS protein by a delX4- or delX5-GUS chimeric gene in roots), as well as being significantly less responsive to salicylic acid and indole acetate application (a 30- to 40-fold lower induction) when compared to the 273 bp prp1-1 promoter, while still retaining a significant fungal responsiveness. Also included in this definition are natural or artificial promoter elements with a DNA sequence that is substantially similar to any of the delX4, delX5, delB34, delB35, and delB51 DNA sequences defined above, i.e., having some nucleotides deleted, replaced or added provided substantially the same promoter characteristics are retained.

In accordance with this invention, a fungus-resistant plant can be produced from a single cell of a plant by transforming the plant cell in a known manner to stably insert, into its nuclear genome, the first chimeric gene of this invention which comprises at least one first foreign DNA that is: under the control of a fungus-responsive promoter comprising at least one fungus-responsive prp1-1 element of this invention, wherein said fungus-responsive promoter does not contain the 273 bp prp1-1 promoter element described in WO 93/19188 or wherein this fungus-responsive promoter has a significantly lower transcription activation in roots and/or upon phytohormone application than the 273 bp prp1-1 promoter of WO 93/19188; and fused at its downstream (i.e., 3') end (or fused downstream of a 3' non-translated trailer sequence) to suitable transcription termination (or regulation) signals, including a polyadenylation signal. Preferably, in the first chimeric gene, a fungus-responsive prp1-1 element is used, in combination with a minimal promoter element such as the 35S minimal promoter.

Thereby, the first RNA and/or protein or polypeptide is produced or overproduced predominantly in those plant cells around, preferably immediately surrounding, a fungal infection site. One or more of these fungus-responsive prp1-1 elements can be present in a promoter, with an endogenous or foreign TATA box, as well as enhancer regions or other pathogen-responsive promoter elements, e.g., the nematode-responsive element described by Opperman et al. (1994). Also, a fungus-responsive prp1-1 element of this invention can also be incorporated in any promoter sequence so as to confer to this promoter the capacity to respond to pathogen, e.g., fungal, infection. For instance, the same or different fungus-responsive prp1-1 elements of this invention can also be linked in multiple consecutive copies to constitute a promoter comprising several fungus-responsive prp1-1 elements of this invention (Benfey et al., 1990).

Optionally, the plant cell genome can also be stably transformed with a second chimeric gene comprising at least one second foreign DNA that is: under the control of the second promoter which is capable of directing expression of the second foreign DNA at least in cells of the plant where the first foreign DNA is expressed, but preferably is repressed in the cells surrounding, more preferably immediately surrounding, the fungal infection site. Alternatively, the second promoter is capable of directing expression of the second foreign DNA substantially selectively in plant cells where expression of the first foreign DNA would result in damage to cells not around, preferably not immediately surrounding, the fungal infection site. The second chimeric gene further comprises suitable transcription termination signals, including a polyadenylation signal. The second chimeric gene is preferably in the same genetic locus as the first chimeric gene, so as to guarantee with a high degree of certainty the joint segregation of both the first and second chimeric genes into offspring of the plant regenerated from the transformed plant cell. However in some cases, such joint segregation is not always desirable, and the second chimeric gene could be in a different genetic locus from the first chimeric gene. When the first foreign DNA, RNA or protein affects plant cell viability (e.g., when the first foreign DNA encodes a barnase protein), even when the fungus-responsive promoter is shown to be selectively or exclusively induced in plant cells immediately surrounding the fungal infection site, it is still preferred that a second DNA, RNA or protein is also expressed in all essential plant cells (e.g., the second DNA will encode the barstar protein when the first foreign DNA encodes the barnase protein), preferably in all plant cells other than those cells surrounding the fungal infection site, so as to prevent any expression of the promoter to negatively affect cells not surrounding the fungal infection site at any moment during plant development.

In the second chimeric gene, the second foreign DNA can also be under the control of a minimal promoter, such as the 35S minimal promoter. "Minimal promoter", as used herein, is a DNA sequence capable of driving a basal level of expression of a coding region, so that some RNA, protein or polypeptide is produced, and comprising at least a TATA-box region, preferably the 35S minimal promoter from nucleotide position −48 to +8 of the 35S gene (Benfey et al., 1990). Typically, a minimal promoter is a DNA sequence recognized by RNA polymerase II, e.g., a TATA-box, but can be any cis-acting DNA sequence allowing minor expression of an RNA in the plant genome. Such a minimal promoter can even be located in plant genomic DNA surrounding the inserted gene, in this case the second chimeric gene even need not contain a plant-expressible promoter.

In accordance with this invention, the first foreign DNA in the first chimeric gene is a DNA fragment that encodes a first RNA and/or protein or polypeptide which, when produced or overproduced in the plant cells surrounding, preferably immediately surrounding, a site of a fungus infection, either: a) kills such surrounding plant cells or at least disturbs significantly their metabolism, functioning and/or development so as to induce an artificial hypersensitive cell death in order to limit the further spread of the invading fungus; and/or b) kills, disables or repels the fungus when it further infects such surrounding plant cells. First foreign DNAs preferably encode, for example, the following which can kill the surrounding plant cells or at least disturb significantly their metabolism, functioning and/or development: RNases such as barnase, RNase T1, RNase SA (SARNase), or binase; toxic proteins such as the Diphteria A toxin (e.g., Palmiter et al., 1987), ricin, or botulin. Potential first foreign DNAs further include DNases such as endonucleases (e.g., EcoRI); proteases such as a papain; enzymes which catalyze the synthesis of phytohormones, such as isopentenyl transferase or the gene products of gene 1 and gene 2 of the T-DNA of Agrobacterium; glucanases; lipases; lipid peroxidases; plant cell wall inhibitors, ribosome-inactivating proteins (e.g., Stirpe et al., 1992) and ribozymes. Other preferred examples of such first foreign DNAs are antisense DNAs encoding RNAs complementary to genes encoding products essential for the metabolism, functioning and/or development of the surrounding plant cells. Such an antisense RNA could be complementary to the endogenous prp1-1 RNA and thus inhibit the action of the produced gluthathione-S-transferase (Hahn and Strittmatter, 1994) at the site of fungal infection.

In a different strategy, wherein the pathogen is more directly killed or negatively affected, the first foreign DNAs encode, for example, the following first polypeptides or proteins which can kill, repel or disable fungi: lytic enzymes, such as chitinases and β-1,3 glucanases, that catalyze the hydrolysis of fungal cell walls; protease inhibitors (Ryan, 1990); fungus-inhibiting ribonucleases (WO 94/18335); and lectins (Broekaert et al, 1989); as well as other plant proteins with antifungal activity, such as the small basic peptide, CMIII, isolated from corn (EP 465 009) and the osmotin-like proteins (EP 460 753 and WO 94/0810), as well as the antifungal peptides from *Amaranthus caudatus* seeds described by Broekaert et al. (1992), the antifungal peptides from *Mirabilis jalapa* seeds described by Cammue et al. (1992), the antifungal P14 proteins described in PCT publication WO 92/20800, the antifungal proteins described in PCT publication WO 94/15961, the antifungal peptides from *Aspergillus giganteus* described in PCT publication WO 91/19738, the basic peptide CMIII from maize seed described in EP 465 009, the Rs-AFP proteins obtained from radish described in PCT patent publication WO 93/05153 and by Terras et al (1992), and genes encoding phytoalexins (Hain et al., 1993). The first foreign DNA can also be a DNA sequence encoding an avirulence gene RNA (e.g., the avr9 gene) and/or the corresponding resistance gene RNA (e.g., the Cf9 gene) as described in PCT patent publication WO 91/15585. In this strategy, a DNA sequence encoding the Cf9 gene product (Jones et al., 1994) can be placed under the control of a fungus-responsive prp1-1 element, such as delX4 of Example 1, and the avr9 coding region (Van Den Ackerveken et al., 1992) can be placed under the control of a fungus-responsive prp1-1 element, or under the control of a wound-induced or a constitutive promoter. In a Cf9-tomato plant, the avr9 coding region could be linked to a promoter comprising the delX4 fungus-responsive element, thus resulting in local necrosis at the fungal infection site. Promoters comprising the newly identified fungus-responsive prp1-1 elements can also drive transcription of an element of another plant-pathogen virulence/avirulence gene combination, or can be applied in any other method for obtaining fungal resistance in plants, e.g., those communicated on the 7th International Symposium on Molecular Plant-Microbe Interactions, University of Edinburgh (see e.g., The Plant Cell, October 1994, pp. 1332–1341). First foreign DNAs can be naturally occurring or can be fully or partially man-made (e.g., synthetic), provided the same protein as originally encoded by the DNA sequence or a protein with substantially the same activity, is encoded. Indeed, since it is known that DNA or RNA sequences can vary significantly without altering the sequence of the encoded protein, it logically follows that DNA or RNA sequences can differ in several nucleotides, without changing significantly the activity or function of that DNA or RNA beyond their normally observed spectrum of biological activity. Also, when high expression of a foreign DNA sequence is desired, certain nucleotides in the DNA may be altered so as to prevent inefficient transcription or translation of that DNA sequence in the foreign host cell.

For some selected plant-pathogen interactions, the fungus-responsive prp1-1 elements of this invention can also drive selective transcription of a DNA encoding an RNA, protein or polypeptide inhibiting a toxin formed by a pathogenic fungus, if the fungal pathogenicity is largely depending on such toxin production. In certain plant-fungus interactions, the production of such fungal toxins is an essential element in pathogenesis (Schäfer, 1994). Similarly, inhibitors of fungal enzymes, detoxifying natural plant antifungal toxins, can be selectively expressed at the site of infection in accordance with this invention. A pathogenic variety of *Gaeumannomyces graminis*, is known to detoxify plant avenacins by means of one fungal enzyme (Schäfer, 1994). Similarly, inhibitors of such a fungal enzyme can be produced or secreted selectively by plant cells to confer resistance to a fungal pathogen. Particularly interesting is the phomalide toxin produced by *Leptosphaeria maculans* (the asexual stage of *Phoma lingam*) on canola plants (Soledade et al., 1993). Strategies could be devised inhibiting toxic action of this pentadepsipeptide selectively at the site of fungal infection.

Alternatively, anti-fungal antibodies can be selectively expressed at the site of fungal infection by the fungus-responsive prp1-1 elements of this invention.

Plants transformed with a first foreign DNA in a first chimeric gene of this invention will be resistant to fungal infection either: because of the plants' fungus-responsive breakdown, in a substantially selective manner, of the plant cells which surround, preferably immediately surround, the fungal infection site, thereby providing a hypersensitive response; or because fungi will be killed, repelled or disabled by, for example, a fungal toxin produced in situ substantially selectively by the plant cells surrounding, preferably immediately surrounding, the fungal infection site.

A preferred fungus-responsive promoter of this invention comprises the delX4 or delX5 fungus-responsive prp1-1 elements of FIG. 1, more preferably the delX4 fungus-responsive prp1-1 element. It is believed that fungus-responsive elements with substantial sequence homology to the fungus-responsive prp1-1 elements of this invention can be identified in the genomic DNA of other plants (e.g., rapeseed, corn, etc.) using the promoter fragments described in Example 1 (and FIG. 1) as hybridization probes in a conventional manner. The increased specificity of the deletion fragments delX4 and delX5 upon fungal infection appears to make these improved promoter portions, as well as similar portions of other members of the prp1 gene family, suitable candidates for providing cis-acting elements which can provide improved specificity of local transcriptional activation in plants upon fungal infection.

Examples of suitable plant-expressible second promoters are: the strong constitutive 35S promoters of the cauliflower mosaic virus of isolates CM 1841 (Gardner et al, 1981), CabbB-S (Franck et al, 1980) and CabbB-JI (Hull and Howell, 1987); the relatively weaker constitutive nos promoter (De Picker et al, 1982); and wound-inducible promoters, such as the TR1' and TR2' promoters which drive the expression of the 1' and 2' genes, respectively, of the T-DNA (Velten et al, 1984). Alternatively, a second promoter can be utilized which is specific for one or more plant tissues or organs (such as leaves), particularly specific tissues or organs (such as roots) not infected by a fungus where the first foreign DNA is nevertheless expressed, whereby the second chimeric gene is expressed only in such specific plant tissues or organs. Another alternative is to use a promoter whose expression is inducible (e.g., by temperature or chemical factors). The second promoter, as used herein, is a promoter that is always directing transcription at a level which is lower than the fungus-responsive or first promoter of this invention in those plant cells around, preferably immediately surrounding, the fungal infection site, upon fungal infection, so that the first foreign DNA is not fully inhibited or inactivated at the site of fungal infection.

In another embodiment of the invention, the second promoter is a fungus-repressed promoter, e.g., an otherwise constitutive plant promoter whose action in controlling transcription is down-regulated or inhibited upon fungal infection in the cells surrounding the fungal infection site, preferably in the cells immediately surrounding the fungal infection site. An example of such a fungus-repressed promoter is the 35S promoter in plants infected with *Botrytis cinerea* (Oral presentation of Dr. R. Hain at the 4th International Congress of Plant Molecular Biology, Amsterdam, Jun. 19–24, 1994).

In accordance with this invention, the second foreign DNA in the second chimeric gene is a DNA fragment that encodes a second RNA and/or protein or polypeptide which, when produced or overproduced in cells of a plant, inhibits or preferably inactivates the first foreign DNA or any first RNA, protein or polypeptide expressed in such cells, particularly where the first RNA, protein or polypeptide would kill or adversely disturb significantly the metabolism, functioning or development of such cells. Second foreign DNAs preferably encode, for example, the following: barstar which neutralizes the activity of barnase (which degrades RNA molecules by hydrolyzing the bond after any guanine residue), binstar which neutralizes the activity of binase, sarstar which neutralizes the activity of sarnase, EcoRI methylase which prevents the activity of the endonuclease EcoRI; or a protease inhibitor which neutralizes the activity of a protease, such as a papain (e.g., papain zymogen and papain active protein), or even an antibody or antibody fragment specifically inactivating a first foreign protein. Another preferred example of a second foreign DNA encodes a strand of an antisense second RNA (as described, for example, in EP 223 399) which would be complementary to a strand of a sense first RNA, such as an antisense RNA inhibiting the activity of a Diphteria, ricin or botulin RNA.

In the first and second chimeric genes of this invention, the 3' transcription termination signals or 3' ends can be selected from amongst those which are capable of providing correct transcription termination and polyadenylation of mRNA in plant cells. The transcription termination signals can be the natural ones of the first and second foreign DNAs, to be transcribed, or can be foreign. Examples of foreign 3' transcription termination signals are those of the octopine synthase gene (Gielen et al, 1984; Ingelbrecht, 1989), the 35S gene (Sanfacon et al, 1991) and of the T-DNA gene 7 (Velten and Schell, 1985).

Also, the chimeric genes of this invention can comprise a native or a foreign intron. Plant introns have been described to increase expression of transgenes, particularly in monocots (Callis et at, 1987). Introns can also be very useful since they prevent proper expression of a gene during the bacterial cloning steps.

The genome of a cell of a plant, particularly a plant capable of being infected with Agrobacterium, can be transformed using a vector that is a disarmed Ti-plasmid containing the first chimeric gene and optionally the second chimeric gene of this invention and carried by Agrobacterium. This transformation can be carried out using the procedures described, for example, in EP 116718, EP 270822, EP 604662 and Gould et al (1991). Preferred Ti-plasmid vectors contain the first and second chimeric genes between the border sequences, or at least located to the left of the right border sequence, of the T-DNA of the Ti-plasmid. Of course, other types of vectors can be used to transform the plant cell, using procedures such as direct gene transfer (as described, for example, in EP 233,247), pollen mediated transformation (as described, for example, in EP 270,356, PCT publication WO 85/01856, and U.S. Pat. No. 4,684,611), plant RNA virus-mediated transformation (as described, for example, in EP 67,553 and U.S. Pat. No. 4,407,956) and liposome-mediated transformation (as described, for example, in U.S. Pat. No. 4,536,475). In case the plant to be transformed is corn, it is preferred that more recently developed methods be used such as, for example, the recent method described in EP 604662 and the method described for certain lines of corn by Fromm et al (1990) and Gordon-Kamm et al (1990) and the method for cereals described in PCT patent publication WO 92/09696. The resulting transformed plant cell can then be used to regenerate a transformed plant in a conventional manner.

It is preferred that the first and second chimeric genes of this invention be inserted in the same genetic locus in a plant genome, preferably in a configuration where interference is minimized between cis-acting elements of the fungus-responsive and second promoters. Preferably, the first and second chimeric genes are each inserted into a plant cell genome in the same genetic locus as a conventional chimeric marker gene. The choice of the marker DNA is not critical (see e.g., Plant Molecular Biology Labfax (1993) for a list of known marker genes). A marker DNA can also encode a protein that provides a distinguishable color to transformed plant cells, such as the A1 gene encoding dihydroquercetin4-reductase (Meyer et al, 1987).

The resulting transformed plant can be used in a conventional breeding scheme to produce more transformed plants with the same characteristics or to introduce the first chimeric gene and optionally the second chimeric gene in other varieties of the same or related plant species or in hybrid plants resulting from a cross with at least one transformed plant of the present invention. Seeds obtained from the transformed plants contain the chimeric gene(s) of this invention as a stable genomic insert.

In another embodiment of this invention, plants transformed with chimeric genes comprising the fungus-responsive prp1-1 elements and driving expression of a selectable or screenable marker DNA, RNA or protein, such as the GUS marker protein (see Examples), can be used to screen for molecules selectively inducing the fungus-responsive prp1-1 elements, as is detected by marker gene expression. These molecules can serve as potential enhancers of the natural resistance to pathogens (Doemer et al., 1990; Kessmann et al., 1994).

The following Examples describe the isolation and characterization of the fungus-responsive prp1-1 elements of this invention and the use of such promoter-effective portions for conferring fungus-resistance to plants. Unless stated otherwise in the Examples, all nucleic acid manipulations are done by the standard procedures described in Sambrook et al, *Molecular Cloning: A Laboratory Manual, Second Edition*, Cold Spring Harbor Laboratory Press, NY (1989) and in volumes 1 and 2 of Ausubel et al., *Current Protocols in Molecular Biology*, Current Protocols, USA (1994). Standard materials and methods for plant molecular work are described in *Plant Molecular Biology Labfax* by R. R. D. Croy, jointly published by BIOS Scientific Publications Limited (UK) and Blackwell Scientific Publications, UK (1993).

In the following Examples, reference is made to the following Sequence Listing:

SEQUENCE LISTING

SEQ ID no. 1 shows the 273 bp DNA sequence of the prp1-1 promoter. The first and last nucleotide of this sequence correspond to positions −402 and −130 of the 273 bp prp1-1 promoter, respectively (Martini et al. 1993).

EXAMPLES

Example 1
Construction of prp1-1 promoter deletion fragments.

Plasmid pBS27-1, which has been described in Martini et al. (1993), contains the promoter sequence of the potato prp1-1 gene covering positions −402 to −130 (presented in SEQ ID No. 1), inserted into the vector pBS(+) (purchased from Stratagene, La Jolla, USA) via BamHI and XbaI restriction sites (the 5'-terminus of the prp1-1 sequence represents a Sau3A site which was ligated with the BamHI site of the vector, the XbaI site was added to the prp1-1 sequence with the help of an XbaI linker, so that the 3' terminus of the prp1-1 sequence could be ligated with the XbaI site of the vector). This plasmid was used as starting material to create deletions of the prp1-1 sequence by treatment with exonuclease III (Double-Stranded Nested Deletion Kit, purchased from Pharmacia, Uppsala, Sweden): for generation of 3' end-terminal deletions, plasmid pBS27-1 was digested with XbaI and afterwards treated with exonuclease III, yielding prp1-1 promoter regions which covers positions 1 to 239 of SEQ ID No. 1 (delX4) and 1 to 153 of SEQ ID No 1 (delX5) (see FIG. 1); after addition of XbaI linkers, the DNAs were recircularized producing plasmids pBS27-1/delX4 and pBS27-1/delX5; for generation of 5'-terminal deletions, plasmid pBS27-1 was cut with BamHI and afterwards treated with exonuclease III treatment, yielding prp1-1 promoter regions covering positions 100 to 273 (delB35), 140 to 273 (delB34) and 176 to 273 (delB51) (FIG. 1); after addition of BamHI linkers DNAs were recircularized resulting in plasmids pBS27-1/delB35, pBS27-1/delB34 and pBS27-1/delB51. The length of the prp1-1 inserts in all plasmids was determined by sequencing (Sanger et al., 1977). Then, the prp1-1 promoter regions were isolated from the plasmids by cutting with EcoRI and XbaI; and inserting into vector pETVgus (Martini et al., 1993) digested with EcoRI and XbaI; thereby, the prp1-1 promoter sequences were located 5' terminal of the CaMV35S TATA-box region (−48 to +8), the coding region of the b-glucuronidase (GUS) gene from *E. coli* and the polyadenylation signal of the pea rbsS-3C gene (Benfey and Chua, 1990), giving plasmids pETVgus27-1/delB35, pETVgus27-1/delB34, pETVgus27-1/delB51, pETVgus27-1/delX4, and pETVgus27-1/delX5. These plasmids were mobilized from *E. coli* strain S17-1 to *Agrobacterium tumefaciens* C58C1-GV3101 harboring helper plasmid pMP90RK (Koncz et al., 1989). Transformation of potato (*Solanum tuberosum* L.) cultivar Désirée was done according to the leaf disc technique outlined by De Block (1988). Appropriately transformed plants were identified by PCR analysis with oligonucleotide primers specific for the GUS gene. Primary regenerants were used to produce tubers, and 4 to 6 weeks old cuttings of tuber grown plants were finally applied in expression studies. Transgenic plants were designated based on the chimeric constructs integrated into the plant genome: DelX4, DelX5, DelB34, DelB35 and DELB51. The length of these fragments and their relative position in the prp1-1 promoter is indicated in FIG. 1.

Example 2
Expression of marker gene/prp1-1 deletion constructs in transgenic potato plants.

Leaves from transgenic potato plants (2 to 7 independent lines per construct) were infected with *Phytophthora infestans* race 1-11 as previously described (Martini et al., 1993); as a control, leaves were treated with water. For stimulation with phytohormones, discs of 0.5 cm diameter were punched out from transgenic leaves with a corkborer and incubated in an aqueous solution containing 1 mM indole-3-acetic acid (IAA) or 10 mM Na-Salicylate (SA), under constant white light at 18° C.; as a control, leaf discs were incubated in water. Leaf material was harvested three days after inoculation with fungal spores or 24 hours after initiation of treatment with phytohormones. The transcriptional activation mediated by the various prp1-1 promoter fragments was determined by measuring b-glucuronidase activity in total protein extracts from this leaf material, according to Jefferson (1987).

Constitutive expression of the chimeric constructs in non-infected roots was assayed by histochemical GUS staining of axenically grown root material from the transgenic lines. Detached roots were vacuum infiltrated with a solution consisting of 100 mM sodium phosphate (pH 7.0) and 0.5 mg/ml X-gluc (5-bromo4-chloro-3-indolyl b-D-glucuronide). The enzymatic reaction was then allowed to proceed for 16 h at 37° C.; afterwards roots were transferred to 70% (v/v) ethanol and evaluated under the microscope.

The induction rates of GUS enzyme activity (measured according to Jefferson, 1987) comparing fungus-infected and water-treated detached leaves, or phytohormone-treated and water-treated leaf discs are listed in Table 1. Additionally, detection of constitutive GUS activity in non-infected roots is indicated in this table. Control constructs comprising only the 35S minimal promoter (lacking a fungus-responsive element), fused to the GUS coding region of this invention, did not produce any detectable amount of GUS enzyme in several tests, either upon infection with *Phytophthora infestans* or phytohormone application. Neither was there found any detectable amount of GUS enzyme in roots. From Table 1, the most interesting line can be chosen, e.g., DelX4-4 or -3, that have a combination of a high fungus-response and a low responsiveness to phytohormone application in combination with no detectable root expression. Line DelB348 is probably defective, since all values are very low.

Example 3
Construction of plant transformation vectors

As described in detail below, the identified fungus-responsive prp1-1 fragments are used to construct first chimeric genes of this invention which are then used; e.g., with second chimeric genes of this invention, to construct plant transformation vectors. A preferred promoter comprises the prp1-1 promoter fragments delX4 or delX5 of Example 1 (FIG. 1), operably linked to a CaMV 35S minimal promoter fragment from nucleotide −48 to nucleotide +8 of the CaMV 35S promoter (Benfey et al., 1990). Each of the promoter fragments is upstream of, and in the same transcriptional unit as, a first foreign DNA encoding barnase from *Bacillus amyloliquefaciens* (Hartley et al., 1988). Downstream of the first foreign DNA is the 3' untranslated end of the nopaline synthase gene ("3'nos") which is isolated as a 260 bp TagI fragment from the nopaline synthase gene (Gielen et al, 1984). This results in a chimeric gene construct that is designated "delX4/35S-barnase-3'nos" and "delX5/35S-barnase-3' nos". These first chimeric genes are introduced between the T-DNA border repeats of the vector pGV941 (Deblaere et al., 1987) as described in PCT publication WO 93/19188. This vector contains a chimeric marker gene containing the nopaline synthase promoter ("pnos"; Depicker et al, 1982), the neo coding region from Tn5 (Beck et al, 1982) and the 3' untranslated end of the octopine synthase gene ("3'ocs"), corresponding to the 706 bp PvuII fragment from the octopine synthase gene (Gielen et al, 1984). The construction of this chimeric "pnos-neo-3'ocs" gene is described by Hain et ai (1985) and in EP 359 617.

In order to construct T-DNA plant transformation vectors carrying also second chimeric genes of this invention, a DNA fragment containing a Pnos-barstar-3'g7 gene construct is introduced in the above described plant vectors, as described in WO 93/19188.

Using the procedure described above, a plant transformation vector is also constructed containing a first chimeric gene, designated "delX4/35S-Rs__AFP2-3'35S", using the DNA coding sequence of the anti-fungal Rs__AFP2 protein described in PCT patent publication WO 93/05153 as first foreign DNA (without "inhibiting" foreign DNA).

Furthermore, following the above outlined procedures, a plant transformation vector, carrying the coding regions of the rice basic chitinase and the b-1,3-glucanase gene of Zhu et al. (1994), each under the control of the delX4/35S promoter construct described above and flanked by the 3' polyadenylation and transcript termination region of the CaMV 35S gene, is also constructed.

Example 4
Transformation of potato and oilseed rape with *Agrobacterium tumefaciens* strains carrying the plant transformation vectors of Example 3

To obtain transformation of, and major expression in, potato and oilseed rape (*Brassica napus*), the plant transformation vectors of Example 3 are each mobilized into the *Agrobacterium tumefaciens* strain C58C1Rif® carrying the avirulent Ti plasmid pGV2260 as described by Deblaere et al (1985). The transconjugants are analyzed by Southern blotting. The respective Agrobacterium strains are used to transform potato plants (*Solanum tuberosum* cvs. Bintje and Désiré) by means of tuber disc infection as described by De Block et al (1987) and oilseed rape using the method described by De Block et al (1989). Transformed calli are selected on medium containing 100 mg/ml kanamycin, and resistant calli are regenerated into plants. For each transformation experiment, about 10 individual transformants are regenerated and analyzed by Southern blotting for gene integration patterns.

Potato and oilseed rape plants transformed with a first chimeric gene comprising a first foreign DNA sequence encoding barnase under the control of the fungus-responsive delX4/35S of delX5/35S promoter of Example 3, and a second chimeric gene comprising a second foreign DNA sequence encoding barstar under the control of the nos promoter show a significantly higher degree of resistance to fungus infection, particularly *Phytophthora infestans* (potato) and *Leptosphaeria maculans* (oilseed rape) infection, than do non-transformed control plants. As a result, the transformed plants have significantly lower yield losses than do the control plants upon statistical analysis of small scale field trials, infected with fungal pathogen. When compared to control plants, fungal sporulation is significantly inhibited even 7 days after infection. Sporulation is followed by examination under the stereoscope, after fungal infection, by applying 20 ml droplets (when using either $2 \times 10^6$ to $5 \times 10^5$ spores/ml) to the bottom side of the potato leaf. After maintenance of the leaves in water, the fungal growth and sporulation can be followed by visual inspection under a stereoscope. The disease resistance phenotype of the transformed plants is confirmed by molecular analysis based on RNA quantification and evaluation of the phenotype in the segregating progeny.

Similar significant reduction of fungal growth is observed on the potato and oilseed rape plants, transformed with the chimeric genes of Example 3, encoding the antifungal chitinase and glucanase, or the antifungal Rs/AFP2 protein.

Needless to say, the use of the fungus-responsive fungus-responsive prp1-1 elements and chimeric genes of this invention is not limited to the transformation of any specific plant(s). Such promoters and chimeric genes can be useful in transforming any crop, such as alfalfa, corn, cotton, sugar beet, brassica vegetables, tomato, soybean, wheat or tobacco, where the promoters can control gene expression, preferably where such expression is to occur abundantly in plant cells which immediately surround fungal infection sites without major induction by wounding, IAA, SA and without significant expression in root tissue.

Also, the use of the improved fungus-responsive promoters of this invention is not limited to the control of particular first foreign DNAs but can be used to control expression of any DNA fragment in a plant.

Furthermore, this invention is not limited to the specific improved fungus-responsive prp1-1 promoter fragments described in the foregoing Examples. Rather, this invention encompasses promoter fragments, equivalent to those of the Examples, such as equivalent promoter fragments of other prp1 genes, which can be used to control the expression of a structural gene, such as a first foreign DNA, at least substantially selectively in plant cells which immediately surround a fungal infection site. Indeed, it is believed that the DNA sequences of the prp1-1 promoter and promoter fragments of the Examples can be modified by replacing some of their nucleotides with other nucleotides, provided that such modifications do not substantially alter the ability of polymerase complexes, including transcription activators, of plant cells, which immediately surround the fungal infection site, to recognize the promoters. Such equivalent fungus-responsive prp1-1 elements preferably have 85%, more preferably 90%, particularly 95% nucleotide sequence similarity with the sequences of the fungus-responsive elements derived from SEQ ID No. 1, such as delX4 and delX5.

Nor is this invention limited to the use of the fungus-responsive chimeric genes of this invention for protecting plants against a Phytophthora fungus such as P. infestans. Such chimeric genes can be used to protect plants against plant-pathogenic fungi, generally, particularly against Phytophthora spp, Pythium spp, Fusarium spp, Sclerotinia spp, Puccinia spp, Ustilago spp, Altemaria spp, Helminthosporium spp, *Sclerotinia sclerotoxiorum, Pyrebioeriza brassicae, Cylindrosporium concentricum, Phoma lingam* and *Leptosphaeria maculans.*

All published documents and patent publications referred to herein are hereby incorporated by reference, i.e. the contents of these documents referred to should be considered as physically incorporated into the above description and examples.

Table 1: Expression pattern of chimeric prp1-1/GUS constructs. The fold-induction of GUS enzyme activity comparing water-treated and stimulated leaves is presented for various independent transgenic lines; values represent averages of three to four independent experiments. GUS enzyme activity in non-infected roots is indicated by "+". Potato line EG2706 harboring the 273-bp prp1-1 promoter portion 5'-terminal of the CaMV 35S TATA-box region (−48 to +8) and the GUS coding region (Martini et al., 1993) was used as a positive control (Pi 1-11: *Phytophthora infestans* race 1-11; IAA: 1 mM indole-3-acetic acid; SA: 10 mM sodium salicylate, nt: not tested)

|          | Pi 1-11 | IAA  | SA   | Root activity |
|----------|---------|------|------|---------------|
| DelX4-1  | 3.5     | 0.9  | 1.0  | —             |
| DelX4-2  | 2.4     | 1.0  | 1.0  | —             |
| DelX4-3  | 9.6     | 0.8  | 0.9  | —             |
| DelX4-4  | 8.4     | 0.8  | 0.9  | —             |
| DelX4-5  | 2.9     | 1.1  | 1.2  | —             |
| DelX5-1  | 2.7     | 0.9  | 0.9  | —             |
| DelX5-2  | 3.3     | 0.9  | 0.7  | —             |
| DelX5-4  | 6.0     | 0.9  | 0.8  | —             |
| DelB34-1 | 7.9     | 23.1 | 20.3 | +             |
| DelB34-6 | 7.0     | 21.2 | 17.9 | +             |
| DelB34-7 | 5.8     | 18.2 | 25.0 | +             |
| DelB34-8 | 1.5     | 1.0  | 0.9  | —             |
| DelB34-9 | 2.7     | 13.3 | 8.5  | nt            |
| DelB34-10| 3.1     | 18.8 | 14.0 | nt            |
| DelB35-1 | 9.3     | 25.3 | 12.6 | +             |
| DelB35-2 | 4.6     | 8.1  | 4.6  | +             |
| DelB51-1 | 8.0     | 10.6 | 6.6  | +             |
| DelB51-2 | 2.8     | 20.1 | 15.8 | +             |
| DelB51-3 | 4.2     | 21.8 | 18.8 | nt            |
| DelB51-4 | 3.4     | 16.7 | 16.9 | nt            |
| DelB51-5 | 1.9     | 1.1  | 0.9  | nt            |
| DelB51-6 | 2.1     | 1.0  | 1.1  | nt            |
| EG2706   | 14.7    | 38.9 | 31.7 | +             |

REFERENCES

ALEXANDER et al. (1993) Proc. Natl. Acad. Sci. USA 90, 7327–7331
BECK et al. (1982) Gene 19, 327–336
BENFEY & CHUA (1990). Science 250, 959–966
BENFEY et al. (1990). The EMBO Journal 9, 1677–1684
BENHAMOU et al. (1993) The Plant Journal 4, 295–305
BOWLES, D. J. (1990) Annu. Rev. Biochem. 59, 873–907
BROEKAERT, W. et al. (1989) Science 245, 1100–1102
BROEKAERT, W. et al. (1992) Biochemistry 31, 4308–4314
CALLIS et al. (1987) Genes & Development 1, 1183–1200
CAMMUE et al. (1992) J. Biol. Chem. 267, 228–2233
COLLINGE, D. B. and SLUSARENKO, A. J. (1987) Plant Mol. Biol. 9, 389–410
CZARNECKA, E. et al. (1984) Plant Mol. Biol. 3, 45–58
DEBLAERE, R. et al. (1987) Methods in Enzymology 153, 277–292
DEBLAERE, R. et al. (1985) Nucleic Acids Research 153, 272–292
DE BLOCK, M. et al. (1987) EMBO J. 6, 2513–2518
DE BLOCK, M. (1988) Theor. Appl. Genet. 76, 767–774
DE BLOCK, M. et al. (1989) P., Plant Physiol. 91, 694–701
DE PICKER et al. (1982) J. Mol. Appl. Genet. 1, 561
DE WIT, P. J. (1987) "Specificity of Active Resistance Mechanisms in Plant-fungus Interactions", pp. 1–25 in G. Pegg and P. Ayres (Eds.), *Fungal Infection of Plants*
DOERNER et al. (1990) Bio/Technology 8, 845
DOUGLAS, D. J. et al. (1991) EMBO J., 10, 1767–1775
FRANCK et al. (1980) Cell 21, 285–294
FRITZEMEIER et al. (1987) Plant Physiol. 85, pp 34–41
FROMM, M. et al. (1990) Bio/Technology 8, 833–839
GARDNER et al. (1981) Nucleic Acids Research 9, 2871–2887
GIELEN, J. et al. (1984) EMBO J. 3, 835–845
GORDON-KAMM, W. et al. (1990) The Plant Cell 2, 603–618
GOULD et al. (1991) Plant Physiology 95, 426–434
HAGEN, G. et al. (1988) J. Biol. Chem. 263, 6442–6446

HAHLBROCK, K. and SCHEEL, D. (1989) Annu. Rev. Plant Physiol. Plant Mol. Biol. 40, 347–369
HAHN and STRITTMATTER (1994) Eur. J. Biochem. 226, 619–626 (1994)
HAIN et al. (1985) Mol. Gen. Genet. 199, 161–168
HAIN et al. (1993) Nature 361, 153
HARTLEY et al. (1988) Journal Mol. Biol. 202, 913–915
HULL and HOWELL (1987) Virology 86, 482–493
INGELBRECHT et al. (1989) The Plant Cell 1, 671–680
JEFFERSON, R. A. (1987) Plant Mol. Biol. Repor. 5, 387–405
JONES, D. A. et al. (1994) Science 266, 789–793
JOOS H. -J. and HAHLBROCK K. (1992) Eur. J. Biochem. 204, 621–629
KESSMANN, H. et al. (1994) Annu. Rev. Phytopath. 32, 439–459
KONCZ C. et al. (1989) Proc. Natl. Acad. Sci. USA 86, 8467–8471
KOMBRINK, E. et al. (1988) Proc. Natl. Acad. Sci. USA 85, 782–786

STERMER, B. A. et al. (1990) Mol. Plant-Microbe Interact. 3, 381–388
STIRPE, F. et al. (1992) Bio/Technology 10, 405–410
TAYLOR, J. L. et al. (1990) Mol. Plant-Microbe Interact 3, 72–77
TERRAS et al. (1992) J. Biol. Chem. 267, 15301–15309
VAN DEN ACKERVEKEN et al. (1992) The Plant J. 2, 359
VAN LOON, L. C. (1985) Plant Mol. Biol. 4, 111–116
VELTEN, J. and SCHELL (1985) J. Nucleic Acids Research 13, 6981–6998
VELTEN, J. et al. (1984) EMBO J. 3, 2723–2730
VIERLING, E. (1991) Annu. Rev. Plant Physiol. Plant Mol. Biol. 42, 579–620
WARD, E. R. et al. (1991) The Plant Cell 3, 1085–1094
ZHU et al. (1994) Bio/Technology 12, 807–812

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: DNA (genomic)

(iv) FEATURE:
        (A) NAME/KEY: misc. feature
        (B) LOCATION: 1..273
        (D) OTHER INFORMATION:/note="273 bp prp1-1 fragment,
                               corresponding to position -402 to -130
                               of the prp1-1 promoter (Martini et al.,
                               1993)"

(xi) SEQUENCE DESCRIPTION: SEQ ID NO:1:

GATCCAAAAT CTAACAATTT AAAAGGTTTT AAATTTTTGT GCTTTTTTTT AAATTAAAAA      60

TATGTCAAAT ATATTAAAAT ATATTTTTTA AATTTTATAC TAAAAAACAT GTCACATGAA     120

TATTTGAAAT TATAAAATTA TCAAAAATAA AAAAAGAATA TTTCTTTAAC AAATTAAAAT     180

TGAAAATATG ATAAATAAAT TAAACTATTC TATCATTGAT TTTTCTAGCC ACCAGATTTG     240

ACCAAACAGT GGGTGACATG AGCACATAAG TCA                                  273

LAMB, C. J. et al. (1989) Cell 56, 215–224
LIU et al. (1994) Proc. Natl. Acad. Sci. USA 91, 1888–1892
MARTINI et al. (1993) Mol. Gen. Genet. 236, 179–186
MEYER et al. (1987) Nature 330, 677–678
OPPERMAN, C. H. et al. (1994) Science 263, 221–223
OSHIMA, M. et al. (1990) The Plant Cell 2, 95–106
PALMITER et al. (1987) Cell 50, 435–443
RYAN, C. A. (1990) Annu. Rev. Phytopathol. 28, 425–449
SANFACON et al. (1991) Genes & Dev. 5, 141–149
SANGER et al. (1977) Proc. Natl. Acad. Sci. US 74, 5463–5467
SCHÄFER, W. (1994) Annu. Rev. Phytopathol. 32, 461–477
SCHMID, J. et al. (1990) The Plant Cell 2, 619–631
SOLEDADE et al. (1993) J. Organ. Chem. 58 (18), 4778–4780

I claim:

1. A fungus-responsive prp1-1 element, consisting of a portion of the DNA sequence of SEQ ID No. 1, which when operably linked to a CaMV 35S TATA-box region, a beta-glucuronidase coding region and a polyadenylation signal of the pea rbsS-3C gene and stably inserted into the nuclear genome of cells of a plant, results in a beta-glucuronidase expression in roots of said plant which is lower than histochemically detectable beta-glucuronidase expression in roots of a control plant obtained by a fungus-responsive prp1-1 element consisting of the DNA sequence of SEQ ID No.1 operably linked with said CaMV 35S TATA-box region, said beta-glucuronidase coding region and said polyadenylation signal of the pea rbsS-3C gene and stably inserted into the nuclear genome of cells of said control plant.

2. A fungus-responsive prp1-1 element, consisting of a portion of the DNA sequence of SEQ ID No. 1, which when operably linked to a CaMV 35S TATA-box region, a β-glucuronidase coding region and a polyadenylation signal of the pea rbsS-3C gene and stably inserted into the nuclear genome of cells of a plant, results in a β-glucuronidase expression whereby the induction of β-glucuronidase expression by phytohormone application is about 2 fold to about 40 fold lower than the induction of the β-glucuronidase expression obtained by a fungus-responsive prp1-1 element consisting of the DNA sequence of SEQ ID No. 1 operably linked with said CaMV 35S TATA-box region, said β-glucuronidase coding region and said polyadenylation signal of the pea rbsS-3C gene and stably inserted into the nuclear genome of cells of a control plant.

3. A fungus-responsive prp1-1 element comprising a portion of about 97 nucleotides to about 239 nucleotides of the DNA sequence of SEQ ID No. 1, provided that said DNA sequence does not comprise the DNA sequence of SEQ ID No. 1 from nucleotide position 1 to nucleotide position 100 or the DNA sequence of SEQ ID No. 1 from nucleotide position 239 to nucleotide position 273.

4. A fungus-responsive prp1-1 element comprising the nucleotide sequence of SEQ ID No. 1 starting from a position between nucleotide position 100 and nucleotide position 176 to nucleotide position 273, provided that said fungus-responsive element is not the DNA sequence of SEQ ID No. 1.

5. A fungus-responsive prp1-1 element comprising the nucleotide sequence of SEQ ID No. 1 from nucleotide position 1 to a position between nucleotide position 153 and nucleotide position 239, provided that said fungus-responsive element is not the DNA sequence of SEQ ID No. 1.

6. A fungus-responsive prp1-1 element which is selected from the group consisting of: the DNA sequence of SEQ ID No. 1 from nucleotide position 1 to nucleotide position 239, the DNA sequence of SEQ ID No. 1 from nucleotide position 1 to nucleotide position 153, the DNA sequence of SEQ ID No. 1 from nucleotide position 100 to nucleotide position 273, the DNA sequence of SEQ ID No. 1 from nucleotide position 140 to nucleotide position 273 and the DNA sequence of SEQ ID No. 1 from nucleotide position 176 to nucleotide position 273.

7. A fungus-responsive prp1-1 element consisting of a nucleotide sequence having 85% to 100% sequence identity with a fungus-responsive prp1-1 element selected from the group consisting of: the DNA sequence of SEQ ID No. 1 from nucleotide position 1 to nucleotide position 239, the DNA sequence of SEQ ID No. 1 from nucleotide position 1 to nucleotide position 153, the DNA sequence of SEQ ID No. 1 from nucleotide position 100 to nucleotide position 273, the DNA sequence of SEQ ID No. 1 from nucleotide position 140 to nucleotide position 273 and the DNA sequence of SEQ ID No. 1 from nucleotide position 176 to nucleotide position 273.

8. A fungus-responsive promoter comprising the fungus-responsive prp1-1 elements of any one of claims 1 to 7, provided that said fungus-responsive element is not the DNA sequence of SEQ ID No.1.

9. The fungus-responsive promoter of claim 8, wherein said fungus-responsive promoter further comprises a minimal promoter element.

10. The fungus-responsive promoter of claim 9, wherein said minimal promoter element is the minimal promoter element of a CaMV35S promoter.

11. A fungus-responsive chimeric gene, comprising the following operably linked elements:
   a) the fungus-responsive promoter of claim 8;
   b) a first foreign DNA that encodes a first RNA or protein or polypeptide which, when produced or overproduced in cells of a plant which immediately surround a fungus-infection site, kills or at least disturbs the metabolism, functioning or development of said plant cells, immediately surrounding said fungus-infection site; and
   c) suitable 3' transcription termination signals for expressing said foreign DNA in said plant cells which immediately surround said fungus infection site.

12. A fungus-responsive chimeric gene, comprising the following operably linked elements:
   a) the fungus-responsive promoter of claim 8;
   b) a first foreign DNA that encodes a first RNA or protein or polypeptide which, when produced or overproduced in cells of a plant which immediately surround a fungus-infection site, kills, disables or repels an infecting fungus; and
   c) suitable 3' transcription termination signals for expressing said foreign DNA in said plant cells which immediately surround said fungus infection site.

13. A plant cell or plant cell culture, each stably transformed with the fungus-responsive chimeric gene of claim 11.

14. A plant cell or plant cell culture, each stably transformed with the fungus-responsive chimeric gene of claim 12.

15. A plant or a seed, each consisting essentially of the plant cells of claim 13.

16. A plant or a seed, each consisting essentially of the plant cells of claim 14.

17. A plant cell comprising the chimeric gene of claim 11, which also comprises a second chimeric gene; said second chimeric gene comprising the following operably linked DNA sequences:
   a) a second promoter which directs transcription of a foreign DNA in all essential plant cells other than those plant cells immediately surrounding said fungus-infection site;
   b) a second foreign DNA that encodes a second RNA or protein or polypeptide which, when produced or overproduced in said other plant cells, inhibits or inactivates the first foreign DNA or the first RNA or protein or polypeptide in said other plant cells; and
   c) suitable 3' transcription termination signals for expressing said second foreign DNA in said other cells of the plant.

18. The plant cell of claim 17, wherein said second promoter is a CaMV 35S promoter or a nopaline-synthase promoter.

19. A plant or a seed, each consisting essentially of the plant cells of claim 17.

20. A process for rendering a plant resistant to fungi comprising the step of transforming the plant's nuclear genome with a chimeric gene of claim 11.

21. A process for rendering a plant resistant to fungi comprising the step of transforming the plant's nuclear genome with a chimeric gene of claim 12.

22. The process of claim 20, wherein said plant is resistant to a fungus selected from the group consisting of Phytophthora spp., Cladosporium spp., Pythium spp., Fusarium spp., Sclerotinia spp., Puccinia spp., Ustilago spp., Alternaria spp., Helminthosporium spp., Septoria spp., Pyrenophora spp., Botrytis spp. and Erysiphe spp.

23. The process of claim 20, wherein said plant is resistant to a fungus selected from the group consisting of *Pyrenoperiza brassicae, Cylindrosporium concentricum, Phomam lingam, Leptosphaeria maculans, Sclerotinia sclerotiorum, Botrytis cinerea, Erysiphe cruciferorum, Peronospora parasitica, Plasmodiophora brassicae* and *Pseudocercosporella capsella.*

24. The process of claim 21, wherein said plant is resistant to a fungus selected from the group consisting of Phytophthora spp., Cladosporium spp., Pythium spp., Fusarium spp., Sclerotinia spp., Puccinia spp., Ustilago spp., Alternaria spp., Helminthosporium spp., Septoria spp., Pyrenophora spp., Botrytis spp. and Erysiphe spp.

25. The process of claim 21, wherein said plant is resistant to a fungus selected from the group consisting of *Pyrenoperiza brassicae, Cylindrosporium concentricum, Phomam lingam, Leptosphaeria maculans, Sclerotinia sclerotiorum, Botrytis cinerea, Erysiphe cruciferorum, Peronospora parasitica, Plasmodiophora brassicae* and *Pseudocercosporella capsella.*

26. A process for combatting plant fungal pathogens, comprising stably transforming a plant cell with the chimeric gene of claim 11 and regenerating a plant from said cell.

27. A process for combatting plant fungal pathogens, comprising stably transforming a plant cell with the chimeric gene of claim 12 and regenerating a plant from said cell.

* * * * *